Jan. 21, 1964 E. S. BOERNER Plant Pat. 2,346
CHRYSANTHEMUM PLANT
Filed Feb. 4, 1963
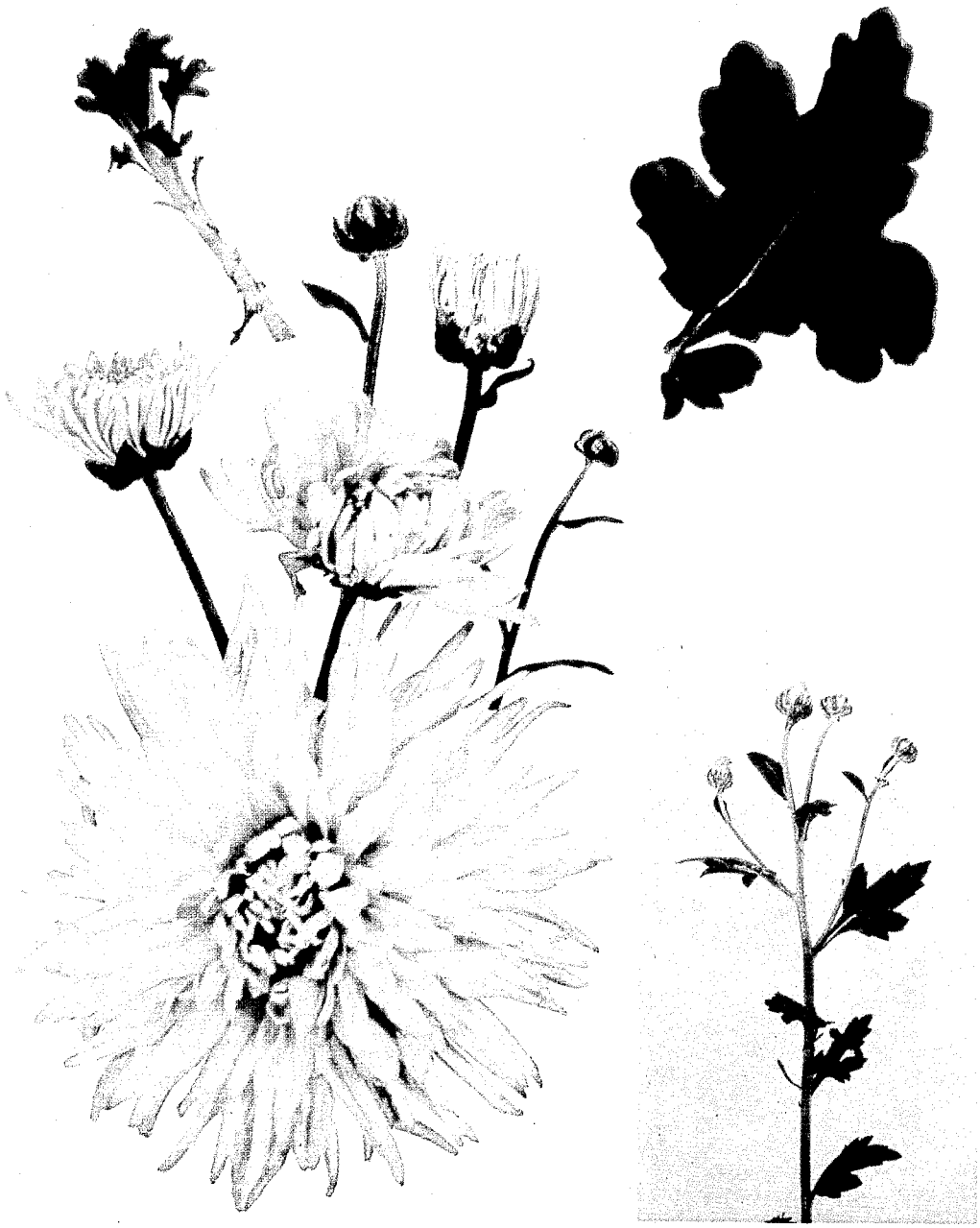
Inventor.
E. S. Boerner
By: Robb & Robb
Attorneys.

United States Patent Office

Plant Pat. 2,346
Patented Jan. 21, 1964

2,346
CHRYSANTHEMUM PLANT

Eugene S. Boerner, Newark, N.Y., assignor to Jackson & Perkins Company, Newark, N.Y., a corporation of New York Filed Feb. 4, 1963, Ser. No. 256,180
1 Claim. (Cl. Plt.—79)

The present invention relates to a new and distinct variety of chrysanthemum plant of the quilled decorative class, which was originated by me by crossing the variety "Sandpiper" (Plant Patent No. 1,932) with an unnamed and unpatented seedling derived from a cross of an unnamed and unpatented Golden Yellow seedling × "Titmouse" (Plant Patent No. 1,630).

The primary objective of this breeding was to produce a new chrysanthemum variety having the vigor and plant habit of the parent variety "Sandpiper," combined with the flower color and flower type of the unnamed seedling parent. This objective was fully achieved, along with other desirable improvements, as evidenced by the following unique combination of characteristics which are outstanding in the new variety and which distinguish it from its parents, as well as from all other varieties of which I am aware:

(1) A vigorous and free plant habit corresponding to the habit of the parent variety "Sandpiper";

(2) Glossy Dark Cress Green foliage;

(3) A quilled decorative flower form; and (4) An attractive and distinct general color tonality of the flowers corresponding to Light Orange-Yellow, very lightly overcast with Capucine Orange.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black-and-white for the purpose of illustrating the form and habit of growth of the stem.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.
*Seed parent.*—"Sandpiper".
*Pollen parent.*—An unnamed seedling of an unnamed Golden Yellow seedling × "Titmouse."
Classification: Quilled decorative.

Growth: Very free; attains height of about 2½ feet.
Cold resistance: Winter hardy in northern New York State.
Blooming period: From middle of September until a hard freeze.

*Flower*

Bud:
*Color.*—When sepals first divide—Yellow Ocher, Plate 15, lightly overcast with Zinc Orange, Plate 15. When petals begin to unfurl—Zinc Orange, Plate 15, with outer edge of petals lightly overcast with Jasper Red, Plate 13. When half-blown—inside: Light Orange-Yellow, Plate 3, lightly overcast with Mikado Orange, Plate 3; outside: Orange-Buff, Plate 3, lightly overcast with Flame Scarlet, Plate 2.
*Peduncle.*—Color—Dark Cress Green, Plate 31. Strength—strong.
Bloom:
*Size.*—5½ inches.
*Stem.*—Strong.
*Form.*—Quilled decorative.
*Petalage.*—Long; quilled.
*Color.*—Center of flower—Light Orange-Yellow, Plate 3, lightly overcast with Flame Scarlet, Plate 2. Outer petals—Light Orange-Yellow, Plate 3, very lightly overcast with Capucine Orange, Plate 3. Base of petals—Chalcedony Yellow, Plate 17. Inside of petals—Deep Chrome, Plate 3, lightly overcast with Cadmium Orange, Plate 3.
*Petals.*—Texture—thin; smooth. Form—quilled.
*Fragrance.*—Very fragrant.

*Plant*

Form: Upright.
Growth: Free.
Foliage:
*Size.*—Large.
*Quantity.*—Normal.
*Color.*—Upper side—Dark Cress Green, Plate 31. Reverse side—Bice Green, Plate 17.
*Texture.*—Leathery; glossy.

I claim:

A new and distinct variety of chrysanthemum plant of the quilled decorative class, substantially as herein shown and described, characterized particularly as to novelty by the unique combination of a vigorous and free plant habit corresponding to that of the parent variety "Sandpiper" (Plant Patent No. 1,932), glossy, Dark Cress Green foliage, a quilled decorative flower form, and a distinctive and attractive general color tonality of the flowers corresponding to Light Orange-Yellow, lightly overcast with Capucine Orange.

No references cited.